(12) United States Patent
Dumanian et al.

(10) Patent No.: US 10,881,394 B2
(45) Date of Patent: Jan. 5, 2021

(54) MESH SUTURE

(71) Applicant: NORTHWESTERN UNIVERSITY, Evanston, IL (US)

(72) Inventors: Gregory Dumanian, Chicago, IL (US); Anandev Gurjala, Chicago, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 266 days.

(21) Appl. No.: 15/703,308

(22) Filed: Sep. 13, 2017

(65) Prior Publication Data

US 2018/0021040 A1 Jan. 25, 2018

Related U.S. Application Data

(63) Continuation of application No. 14/976,864, filed on Dec. 21, 2015, which is a continuation of application (Continued)

(51) Int. Cl.
*A61B 17/06* (2006.01)
*A61L 17/00* (2006.01)
(Continued)

(52) U.S. Cl.
CPC ........ *A61B 17/06166* (2013.01); *A61B 17/06* (2013.01); *A61L 17/00* (2013.01);
(Continued)

(58) Field of Classification Search
CPC . A61B 17/0401; A61B 17/0469; A61B 17/06; A61B 17/06166; A61B 2017/0409; A61B 2017/0412; A61B 2017/0414; A61B 2017/0446; A61B 2017/0458; A61B 2017/0461; A61B 2017/0464; A61B 2017/0495; A61B 2017/0608; A61B 2017/061; A61B 2017/06171;
(Continued)

(56) References Cited

U.S. PATENT DOCUMENTS 3,037,619 A  6/1962  Stevens
3,304,557 A  2/1967  Polansky
(Continued)

FOREIGN PATENT DOCUMENTS

CN  1547455 A  11/2004
CN  1652826 A  8/2005
(Continued)

OTHER PUBLICATIONS

Australian Patent Application No. 2017261502, Examination Report No. 1, dated Dec. 12, 2018.
(Continued)

*Primary Examiner* — Wade Miles
*Assistant Examiner* — Kankindi Rwego
(74) *Attorney, Agent, or Firm* — Merchant & Gould P.C.

(57) ABSTRACT

A medical device includes a surgical needle attached to an elongated mesh suture. The suture is constructed of macroporous flat wall that facilitates and allows tissue integration into the suture core subsequent to introduction to the body, thereby preventing suture pull-through and improving biocompatibility.

7 Claims, 4 Drawing Sheets

Related U.S. Application Data

No. 13/713,665, filed on Dec. 13, 2012, now Pat. No. 9,237,889.

(60) Provisional application No. 61/602,183, filed on Feb. 23, 2012.

(51) Int. Cl.
　　*A61B 17/04*　　　　(2006.01)
　　*A61B 17/00*　　　　(2006.01)

(52) U.S. Cl.
　　CPC ............ *A61B 2017/00526* (2013.01); *A61B 2017/0412* (2013.01); *A61B 2017/0417* (2013.01); *A61B 2017/0461* (2013.01); *A61B 2017/0464* (2013.01); *A61B 2017/061* (2013.01); *A61B 2017/0608* (2013.01); *A61B 2017/06185* (2013.01); *Y10T 29/49826* (2015.01)

(58) Field of Classification Search
　　CPC .. A61B 2017/06176; A61B 2017/0618; A61B 2017/06185; A61B 2017/0619; A61F 2/0045; A61F 2/0063; A61F 2/0077; A61F 2002/0068; A61F 2002/0072; B01D 69/08
　　See application file for complete search history.

(56) References Cited

U.S. PATENT DOCUMENTS

| | | | |
|---|---|---|---|
| 3,316,557 A | | 5/1967 | Liebig |
| 3,514,791 A | | 6/1970 | Sparks |
| 3,918,455 A | * | 11/1975 | Coplan ............ A61B 17/06004 606/225 |
| 4,034,763 A | | 7/1977 | Frazier |
| 4,372,293 A | | 2/1983 | Vijil-Rosales |
| 4,392,495 A | | 7/1983 | Bayers |
| 4,510,934 A | | 4/1985 | Batra |
| 4,712,553 A | | 12/1987 | MacGregor |
| 4,880,002 A | | 11/1989 | MacGregor |
| 5,280,674 A | | 1/1994 | Granger et al. |
| 5,382,257 A | | 1/1995 | Lewis et al. |
| 5,423,821 A | | 6/1995 | Pasque |
| 5,450,860 A | * | 9/1995 | O'Connor ............ A61B 17/06 128/898 |
| 5,645,568 A | | 7/1997 | Chervitz et al. |
| 5,879,371 A | | 3/1999 | Gardiner et al. |
| 5,899,909 A | | 5/1999 | Claren et al. |
| 5,984,333 A | | 11/1999 | Constantijn et al. |
| 5,984,933 A | | 11/1999 | Yoon |
| 6,143,029 A | | 11/2000 | Rippstein |
| 6,296,659 B1 | | 10/2001 | Foerster |
| 6,315,788 B1 | | 11/2001 | Roby |
| 6,406,423 B1 | * | 6/2002 | Scetbon ............ A61B 17/0469 128/898 |
| 6,475,139 B1 | * | 11/2002 | Miller ................ A61B 1/00087 600/135 |
| 6,478,727 B2 | | 11/2002 | Scetbon |
| 6,620,185 B1 | | 9/2003 | Harvie et al. |
| 6,638,211 B2 | | 10/2003 | Suslian et al. |
| 6,814,741 B2 | | 11/2004 | Bowman et al. |
| 6,911,003 B2 | | 6/2005 | Anderson et al. |
| 6,981,944 B2 | | 1/2006 | Jamiolkowski et al. |
| 7,481,826 B2 | | 1/2009 | Cichocki, Jr. |
| 7,547,316 B2 | | 6/2009 | Priewe et al. |
| 7,621,864 B2 | | 11/2009 | Suslian et al. |
| 7,658,751 B2 | | 2/2010 | Stone et al. |
| 7,740,646 B2 | | 6/2010 | Hunt et al. |
| 7,815,562 B2 | | 10/2010 | Chu |
| 7,875,055 B2 | | 1/2011 | Cichocki, Jr. |
| 8,047,982 B2 | | 11/2011 | Kammerer |
| 8,062,363 B2 | | 11/2011 | Hirpara et al. |
| 8,128,656 B2 | | 3/2012 | Cichocki |
| 8,202,306 B2 | | 6/2012 | Dreyfuss |
| 8,257,393 B2 | | 9/2012 | Cichocki, Jr. |
| 8,273,011 B2 | | 9/2012 | Browning |
| 8,298,247 B2 | | 10/2012 | Sterrett et al. |
| 8,574,149 B2 | | 11/2013 | Evans et al. |
| 8,613,755 B1 | | 12/2013 | Foerster |
| 9,237,889 B2 | | 1/2016 | Dumanian et al. |
| 10,278,694 B2 | | 5/2019 | Dumanian |
| 2002/0107430 A1 | | 8/2002 | Neisz et al. |
| 2003/0050530 A1 | | 3/2003 | Neisz et al. |
| 2003/0149447 A1 | | 8/2003 | Morency et al. |
| 2004/0054253 A1 | | 3/2004 | Snitkin et al. |
| 2004/0144394 A1 | | 7/2004 | Dauner et al. |
| 2005/0028304 A1 | | 2/2005 | Becker |
| 2005/0119696 A1 | * | 6/2005 | Walters ............ A61B 17/06166 606/228 |
| 2005/0192631 A1 | | 9/2005 | Grafton |
| 2005/0277985 A1 | | 12/2005 | Wert et al. |
| 2005/0283040 A1 | | 12/2005 | Greenhalgh |
| 2006/0229675 A1 | | 10/2006 | Novoa et al. |
| 2007/0068538 A1 | | 3/2007 | Anderson et al. |
| 2008/0034801 A1 | | 2/2008 | Canham et al. |
| 2008/0051833 A1 | | 2/2008 | Gramuglia et al. |
| 2008/0082113 A1 | | 4/2008 | Bishop et al. |
| 2008/0119880 A1 | | 5/2008 | Chu |
| 2008/0207989 A1 | | 8/2008 | Kaleta et al. |
| 2008/0294193 A1 | | 11/2008 | Schwartz et al. |
| 2009/0012560 A1 | | 1/2009 | Hunter et al. |
| 2009/0112258 A1 | | 4/2009 | Kreidler |
| 2009/0182375 A1 | | 7/2009 | Isse et al. |
| 2009/0192347 A1 | * | 7/2009 | Davila ............ A61B 17/06109 600/37 |
| 2009/0216326 A1 | | 8/2009 | Hirpara et al. |
| 2009/0248071 A1 | | 10/2009 | Saint et al. |
| 2009/0318962 A1 | | 12/2009 | Spedden et al. |
| 2010/0005685 A1 | | 1/2010 | Russell |
| 2010/0056857 A1 | | 3/2010 | Nordmeyer |
| 2010/0063599 A1 | | 3/2010 | Brunelle et al. |
| 2010/0241141 A1 | | 9/2010 | Lee |
| 2011/0010803 A1 | | 1/2011 | Zank et al. |
| 2011/0046669 A1 | | 2/2011 | Goraltchouk et al. |
| 2011/0054524 A1 | | 3/2011 | Beevers et al. |
| 2011/0106153 A1 | | 5/2011 | Stone et al. |
| 2011/0108039 A1 | * | 5/2011 | Frigstad .................... A61F 6/22 128/831 |
| 2011/0137419 A1 | | 6/2011 | Wong |
| 2011/0282384 A1 | | 11/2011 | Odermatt et al. |
| 2011/0319932 A1 | | 12/2011 | Avelar et al. |
| 2012/0065732 A1 | | 3/2012 | Roller et al. |
| 2012/0083649 A1 | | 4/2012 | Suslian et al. |
| 2012/0136388 A1 | | 5/2012 | Odermatt et al. |
| 2012/0215063 A1 | * | 8/2012 | Holsten ................ A61F 2/0045 600/37 |
| 2012/0245629 A1 | * | 9/2012 | Gross ............... A61B 17/06166 606/228 |
| 2013/0178699 A1 | | 7/2013 | Saint et al. |
| 2013/0226232 A1 | | 8/2013 | Dumanian et al. |
| 2016/0106423 A1 | | 4/2016 | Dumanian et al. |
| 2018/0000480 A1 | | 1/2018 | Dumanian et al. |
| 2018/0042608 A1 | | 2/2018 | Dumanian et al. |
| 2018/0078255 A1 | | 3/2018 | Dumanian |
| 2018/0360453 A1 | | 12/2018 | Dumanian et al. |
| 2019/0192142 A1 | | 6/2019 | Dumanian |

FOREIGN PATENT DOCUMENTS

| | | |
|---|---|---|
| CN | 200980691 Y | 11/2007 |
| CN | 101321498 A | 12/2008 |
| CN | 101380484 A | 3/2009 |
| CN | 101401435 A | 4/2009 |
| CN | 101431947 A | 5/2009 |
| CN | 201691977 U | 1/2011 |
| CN | 201759610 U | 3/2011 |
| CN | 102076280 A | 5/2011 |
| CN | 102076580 A | 5/2011 |
| CN | 104168840 A | 11/2014 |
| CN | 104224253 A | 12/2014 |
| EP | 0490143 A2 | 6/1992 |

(56) References Cited

FOREIGN PATENT DOCUMENTS

| | | |
|---|---|---|
| EP | 0887045 A1 | 12/1998 |
| EP | 1060714 A2 | 12/2000 |
| EP | 1844735 A2 | 10/2007 |
| EP | 2774579 A1 | 9/2014 |
| GB | 2458878 A | 10/2009 |
| GB | 2464952 A | 5/2010 |
| GB | 2468307 A | 9/2010 |
| JP | 2006-025867 A | 2/2006 |
| JP | 2011-525411 A | 9/2011 |
| JP | 2015501186 A | 1/2015 |
| JP | 2015511160 A | 4/2015 |
| JP | 2017213397 A | 12/2017 |
| KR | 2010-0030009 A | 3/2010 |
| KR | 1020190006031 A | 1/2019 |
| KR | 1020200006191 A | 1/2020 |
| WO | WO-9617544 A2 | 6/1996 |
| WO | WO-02087610 A1 | 11/2002 |
| WO | WO-03022161 A1 | 3/2003 |
| WO | WO-03092727 A1 | 11/2003 |
| WO | WO2004030517 A2 | 4/2004 |
| WO | WO-2005/007019 A2 | 1/2005 |
| WO | WO-2006/084165 A2 | 8/2006 |
| WO | WO2010008815 A1 | 1/2010 |
| WO | WO-2010/028197 A1 | 3/2010 |
| WO | WO2010051506 A1 | 5/2010 |
| WO | WO-2010100488 A1 | 9/2010 |
| WO | WO2011022515 A1 | 2/2011 |
| WO | WO2011025760 A1 | 3/2011 |
| WO | WO2013126130 A1 | 8/2013 |
| WO | WO-2016148904 A1 | 9/2016 |

OTHER PUBLICATIONS

European Patent Application No. 18155913.9, Extended European Search Report, dated Jun. 5, 2018.
International Search Report for International Patent Application PCT/US2018/039243, dated Oct. 10, 2018.
Written Opinion for International Patent Application PCT/US2018/039243, dated Oct. 10, 2018.
Anderson, Biological responses to materials, Ann. Rev. Mater. Res., 31:81-110 (2001).
Anderson, Inflammation, Wound Healing, and the Foreign-Body Response. Chapter 11.2.2, pp. 503-513, In: Ratner et al. (eds.), Biomaterials Science, An Introduction to Materials in Medicine, 3rd., Elsevier (2013).
Bellon et al., Effect of relaparotomy through previously integrated polypropylene and polytetrafluoroethylene experimental implants in the abdominal wall, J. Am. Coll. Surg., 188:466-72 (1999).
Bellon et al., Integration of biomaterials implanted into abdominal wall: process of scar formation and macrophage response, Biomaterials, 15:381-7 (1995).
Berger et al., Healing of arterial prostheses in man: its incompleteness, Ann. Surg., 175:118-27.
Bobryshev et al., Colonisation of prosthetic grafts by immunocompetent cells in a sheep model, Cardiovascular Surgery, 9(2):166-76 (2001).
Brewster, Chapter 37, Prosthetic Grafts, pp. 559-578 In: Rutherford, Vascular Surgery, Philadelphia: Saunders Co. (1995).
Brown et al., Which mesh for hernia repair, Ann. R. Coll. Surg. Engl., 92:272-8 (2010).
Clowes et al., Mechanisms of arterial graft healing, Am. J. Pathol., 123:220-30 (1986).
Cobb et al., Textile analysis of heavy weight, mid-weight, and light weight polypropylene mesh in porcine ventral hernia model, J. Surg. Res., 136:1-7 (2006).
Conze et al., New polymer for intra-abdominal meshes—PVDF copolymer, J. Biomed. Mater. Res. Part B: App. Biomater., 87B:321-8 (2008).
Conze et al., Polypropylene in the intra-abdominal position: influence of pore size and surface area, Hernia, 8:365-72 (2004).
Debakey et al., The fate of Dacron vascular grafts, Arch. Surg., 89:757-82 (1964).
Deeken et al., Physicomechanical evaluation of polypropylene, polyester, and polytetrafluoroethylene meshes for inguinal hernia repair, J. Am. Coll. Surg., 212:68-79 (2011).
Franz, The biology of hernia formation, Surg. Clin. N. Am., 88:1-15 (2008).
Golden et al., Healing of polytetrafluoroethylene arterial grafts is influenced by graft porosity, J. Vasc. Surg., 11:838-45 (1990).
Hake et al., Healing parameters of a new albumin-coated knitted Dacron graft, Thorac. Cardiovasc. Surgeon, 39:208-13 (1991).
International Search Report for Application No. PCT/US2012/069480 dated Mar. 8, 2013.
Kaiser, Alloplastic replacement of canine trachea with Dacron, Thorac. Cardiovasc. Surg., 33:239-43 (1985).
Klinge et al., "The ideal mesh?", Pathobiology, 80:169-75 (2013).
Klinge et al., Impact of polymer pore size on the interface scar formation in a rat model, J. Surg. Res., 103:208-14 (2002).
Klinge et al., Modified classification of surgical meshes for hernia repair based on the analyses of 1000 explanted meshes, Hernia, 16:251-8 (2012).
Ko et al., "Components Separation" technique for the treatment of complex abdominal wall defects: An 11-year experience with 200 patients, Arc. Surg., 144:1047-55 (2009).
Lista et al., Subglandular breast augmentation with textured, anatomic, cohesive silicone implants: a review of 440 consecutive patients, Plastic Reconstr. Surg., 132:295-303 (2013).
Mathisen et al., The influence of denier and porosity on performance of a warp-knit Dacron arterial prosthesis, Bob Hope International Heart Research Institute, vol. 203, No. 4, pp. 382-389 (1985).
McLeod et al., Does the size of the stitch length affect surgical site infection?, J. Am. Coll. Surg., pp. 556-560 (2013).
Mühl et al., "New Objective Measurement to Characterize the Porosity of Textile Implants," Journal of Biomedical Materials Research Part B: Applied Biomaterials, Mar. 23, 2007, 8 pages.
Nakayama et al., In vivo tissue-engineered small-caliber arterial graft prosthesis consisting of autologous tissue (biotube), Cell Transplantation, 13:439-49 (2004).
Orenstein et al., Comparative analysis of histopathologic effects of synthetic meshes based on material, weight, adn pore size in mice, J. Surg. Res., 176:423-9 (2012).
Pascual et al., Early tissue incorporation and collagen deposition in lightweight polypropylene meshes: bioassay in an experimental model of ventral hernia, Surgery, 144:427-35 (2008).
Poulose et al., Epidemiology and cost of ventral hernia repair: making the case for hernia research, Hernia, 16:179-83 (2012).
Sauvage et al., Interspecies healing of porous arterial prostheses, Arch. Surg., pp. 698-705 (1974).
Smooth Breast Implants vs. Textured Breast Implants—Which should I choose?, downloaded from the Internet at <http://www.implantinfo.com/faqs/1.49.aspx> on Sep. 20, 2013.
Sparks, Die-Grown reinforced arterial grafts: observations on long-term animal grafts and clinical experience, Ann. Surgery, pp. 787-794 (Nov. 1970).
Spear et al., Late seromas after breast implants: theory and practice, Plast. Reconstr. Surg., 130:423-35 (2012).
Tsuchida et al., Healing mechanisms of PTFE grafts: significance of transmural structure, J. Surg. Res., 71:187-95 (1997).
Tsukada et al., Experimental study of a new tracheal prosthesis: pored Dacrob tube, J. Thorac. Cardiovasc. Surg., 127:877-84 (2004).
Weslowski et al., Porosity: Primary determinant of ultimate fate of synthetic vascular grafts, Surgery, 50:91 (1961).
White, The effect of porosity and biomaterial on the healing and long-term mechanical properties of vascular prostheses, ASAIO Trans., 34:95-100 (1988).
Wilson, Vascular Access: Principles and Practice, 5th ed., pp. pp. 65-68 (2010).
Written Opinion for Application No. PCT/US2012/069480 dated Mar. 8, 2013.
Sweat, et al., "Polypropylene Mesh Tape for Stress urinary Incontinence: Complications of Urethral Erosion and Outlet Obstruction", The Journal of Urology, vol. 168, 144-146, Jul. 2002.
Morton, et al., "Urethral injury associated with minimally invasive mid-urethral sling procedures for the treatment of stress urinary incontinence: a case series and systematic literature search", The

(56) References Cited

OTHER PUBLICATIONS

Authors Journal complilation, BJOG An International Journal of Obstetrics and Gynaecology, 1120-1126 2009.
Huang, et al., "Management of polypropylene mesh erosion after intravaginal midurethral sling operation for female stress urinary incontinence", International Urogynecologyy Journal, 437-440, 2005.
Houshang Seradge, M.D., "Elongation of the repair configuration following flexor tendon repair", The Journal of Hand Surgery, vol. 8, No. 2, 182-185, Mar. 1983.
Klinge, et al., "Modified classification of surgical meshes for hernia repair based on teh analyses of 1,000 explanted meshes", Springerlink.com, Hernia (2012) 16:251-258, May 2012.
Armañanzas, et al., "Prophylactic Mesh vs Suture in the Closure of the Umbilical Trocar Site after Laparoscopic Cholecystectomy in High-Risk Patients for Incisional Hernia. A Randomized Clinical Trial", ISSN 1072-7515/14, The American College of Surgeons, vol. 218, No. 5, May 2014.
Burger, et al., "Incisional Hernia: Early Complication of Abdominal Surgery", World Journal of Surgery, (2005) 29: 1608-1613.
Xing et al., "Early laparotomy wound failure as the mechanism for incisional hernia formation", Journal of Surgical Research, www.sciencedirect.com, E35-E42, 2012.
Bevoni, et al., "Long term results of acute achilles repair with triple-bundle technique and early rehabilitation protocol", Injury , Int. J. Care Injured 45 (2014) 1268-1274.
International Preliminary Report on Patentability, Written Opinion for Application No. PCT/US2012/069480 dated Sep. 4, 2014.
Dumanian, et al., "Experimental Study of the Characteristics of a Novel Mesh Suture", British Journal of Surgery, Wiley Online Library, DOI: 10.1002/bjs.9853, Apr. 8, 2015.
Souza, M.D., et al., "In Vivo Evaluation of a Novel Mesh Suture Design for Abdominal Wall Closure", Division of Plastic Surgery, Northwestern University Feinberg School of Medicine, DOI: 10.1097/prs.0000000000000910, Apr. 11, 2014.
Office Action, Chinese Application No. 201280070639.6, dated Feb. 26, 2016.
International Preliminary Report on Patentability and Written Opinion for International Application No. PCT/US2016/020231, dated Sep. 19, 2017.
Office Action for Application No. JP 2014-558731, dated Feb. 7, 2017.
Extended European Search Report for European Application No. 17197004.9 dated Feb. 14, 2018.
International Search Report and Written Opinion for International Application No. PCT/US2018/039243, dated Oct. 10, 2018.
Dirk Weyhe et al., "Large pore size and controlled mesh elongation are relevant predictors for mesh integration quality and low shrinkage—Systematic analysis of key parameters of meshes in a novel minipig hernia model", International Journal of Surgery, vol. 22, Oct. 1, 2015, pp. 46-53, XP055511014.
Office Action for Application No. JP 2017-148672, dated Aug. 31, 2018.
Non-final Office Action for U.S. Appl. No. 15/825,960, dated Aug. 31, 2018.
Chinese Patent Application No. 201880003637.2, First Office Action and Search Report, dated Sep. 18, 2019.
U.S. Appl. No. 15/556,831, Nonfinal Office Action, dated Oct. 30, 2019.
Korean Patent Application No. 10-2019-7008610, Office Action, dated Oct. 8, 2019.
Canadian Patent Application No. 2865278, Office Action, dated Jul. 26, 2018.
European Patent Application No. 18742649.9, Communication Pursuant to Article 94(3) EPC, dated Jun. 7, 2019.
Israel Patent Application No. 234126, Office Action, dated Mar. 19, 2018.
Israel Patent Application No. 265173, Office Action, dated Sep. 9, 2019.
Japanese Patent Application No. 2017-547562, Notice of Reasons for Rejection, dated Sep. 3, 2019.
Korean Patent Application No. 10-2014-7026080, Office Action, dated Mar. 20, 2018.
U.S. Appl. No. 15/703,185, Nonfinal Office Action, dated Aug. 19, 2019.
U.S. Appl. No. 14/976,864, Nonfinal Office Action, dated Jun. 6, 2019.
Australian Patent Application No. 2016233740, Examination Report No. 1, dated Nov. 1, 2019.
Brazilian Patent Application No. BR11201420564-7, Search Report, dated Nov. 5, 2019.
Chinese Patent Application No. 201680011861.7, First Office Action and Search Report, dated Oct. 16, 2019.
European Patent Application No. 18742649.9, Communication Pursuant to Article 94(3) EPC, dated Nov. 29, 2019.
Japanese Patent Application No. 2019-511390, Office Action, dated Nov. 19, 2019.
Horeman et al., "Force Sensing in Surgical Sutures", PLOS ONE, vol. 8, Issue 12, Dec. 2013.
Mioton et al., "Theoretic and Evidence-based Laparotomy Closure with Sutures and Meshes", Plastic and Reconstructive Surgery, vol. 142, No. 3S, Sep. 2018.
DuBay et al., "Incisional herniation induces decreased abdominal wall compliance via oblique muscle atrophy and fibrosis," Ann Surg. Jan. 2007;245(1):140-146.
Petter-Puchner AH, "The State of Midline Closure of The Abdominal Wall", British Journal of Surgery 102: 1446-1447, 2015.
International Search Report and Written Opinion of the International Searching Authority for Application No. PCT/US2016/020231, dated May 23, 2016, 11 pages.

* cited by examiner

MESH SUTURE

CROSS-REFERENCE TO RELATED APPLICATIONS

This Application is a Continuation of U.S. application Ser. No. 14/976,864, filed Dec. 21, 2015, which is a Continuation of U.S. application Ser. No. 13/713,665, filed Dec. 13, 2012, now U.S. Pat. No. 9,237,889, which claims the priority benefit of U.S. Provisional Application 61/602,183, filed Feb. 23, 2012. The entire content of each of the foregoing applications is incorporated herein by reference.

FIELD OF THE DISCLOSURE

The present disclosure provides sutures with increased surface area and/or tissue integrative properties and methods of use and manufacture thereof. In particular, provided herein are sutures with cross-section profiles and other structural characteristics that strengthen closure, prevent suture pull-through, and/or resist infection, and methods of use thereof.

BACKGROUND

One of the foundations of surgery is the use of suture to re-appose tissue, i.e., to hold tissue in a desired configuration until it can heal. In principle, suturing constitutes introducing a high tensile foreign construct (looped suture) into separate pieces of tissue in order to hold those pieces in close proximity until scar formation can occur, establishing continuity and strength between tissues. Sutures initially provide the full strength of the repair, but then become secondarily reinforcing or redundant as the tissue heals. The time until tissue healing reaches its maximal strength and is dependent on suture for approximation, therefore, is a period of marked susceptibility to failure of the repair due to forces naturally acting to pull the tissues apart.

Conventional sutures provide a circular or single-point cross-sectional profile extended over the length of the suture material. Such a suture has the great benefit of radial symmetry, which eliminates directional orientation, allowing the user (e.g., physician, surgeon, medic, etc.) to not have to worry about orienting the suture during use. However, a considerable disadvantage of the currently used single-point cross-section is that it does not effectively distribute force, and actively concentrates force at a geometric point (e.g., the point at the leading edge of the circle) creating a sharp edge in the axial dimension. Under these conditions, the tissue is continuously exposed to tension, increasing the likelihood that stress concentration at a geometric point or sharp edge will cut through the tissue.

Indeed, studies of surgical closures, a most prominent example being hernia repairs, demonstrate that the majority of failures or dehiscences occur in the early post-operative period, in the days, weeks, or months immediately following the operation, before full healing can occur. Sutures used to close the abdominal wall have high failure rates as demonstrated by the outcome of hernia formation. After a standard first-time laparotomy, the postoperative hernia occurrence rate is between 11-23%. The failure rate of sutures after hernia repair is as high as 54%. This is a sizeable and costly clinical problem, with approximately 90,000 post-operative hernia repairs performed annually in the United States. Surgical failures have been blamed on poor suture placement, suture composition, patient issues such as smoking and obesity, and defects in cellular and extracellular matrices. Clinical experience in examining the cause of these surgical failures reveals that it is not breakage of suture as is commonly thought; in the majority of cases the cause is tearing of the tissue around the suture, or from another perspective, intact stronger suture cutting through weaker tissue. Mechanical analysis of the suture construct holding tissue together shows that a fundamental problem with current suture design is stress concentration at the suture puncture points through the tissue. That is, as forces act to pull tissues apart, rather than stress being more evenly distributed throughout the repair, it is instead concentrated at each point where the suture pierces through the tissue. The results are twofold: (1) constant stress at suture puncture points causes sliding of tissue around suture and enlargement of the holes, leading to loosening of the repair and an impairment of wound healing, and (2) at every puncture point where the stress concentration exceeds the mechanical strength of the tissue, the suture slices through the tissue causing surgical dehiscence. In addition, high pressure on the tissue created during tightening of the surgical knot can lead to local tissue dysfunction, irritation, inflammation, infection, and in the worst case tissue necrosis. This tissue necrosis found within the suture loop is one additional factor of eventual surgical failure.

There has been no commercial solution to the aforementioned problems with conventional sutures. Rather, thinner sutures continue to be preferred because it is commonly thought that a smaller diameter may minimize tissue injury. However, the small cross-sectional diameter in fact increases the local forces applied to the tissue, thereby increasing suture pull-through and eventual surgical failure.

One alternative to the conventional suture is disclosed by Calvin H. Frazier in U.S. Pat. No. 4,034,763. The Frazier patent discloses a tubular suture manufactured from loosely woven or expanded plastic material that has sufficient microporosity to be penetrated with newly formed tissue after introduction into the body. The Frazier patent does not expressly describe what pore sizes fall within the definition of "microporosity" and moreover it is not very clear as to what tissue "penetration" means. The Frazier patent does, however, state that the suture promotes the formation of ligamentous tissue for initially supplementing and then ultimately replacing the suture's structure and function. Furthermore, the Frazier patent describes that the suture is formed from Dacron or polytetrafluoroethylene (i.e., Teflon®), which are both commonly used as vascular grafts. From this disclosure, a person having ordinary skill in the art would understand that the suture disclosed in the Frazier patent would have pore sizes similar to those found in vascular grafts constructed from Dacron or Teflon®. It is well understood that vascular grafts constructed of these materials serve to provide a generally fluid-tight conduit for accommodating blood flow. Moreover, it is well understood that such materials have a microporosity that enables textured fibrous scar tissue formation adjacent to the graft wall such that the graft itself becomes encapsulated in that scar tissue. Tissue does not grow through the graft wall, but rather, grows about the graft wall in a textured manner. Enabling tissue in-growth through the wall of a vascular graft would be counterintuitive because vascular grafts are designed to carry blood; thus, porosity large enough to actually permit either leakage of blood or in-growth of tissue, which would restrict or block blood flow, would be counterintuitive and not contemplated. As such, these vascular grafts, and therefore the small pore sizes of the microporous suture disclosed in the Frazier patent, operate to discourage and prevent normal neovascularization and tissue in-growth into the suture. Pore sizes less than approximately 200 microns are known to be watertight and disfavor neovascularization. See, e.g., Mühl et al., New Objective Measurement to Characterize the Porosity of Textile Implants, Journal of Biomedical Materials Research Part B: Applied Biomaterials DOI 10.1002/jbmb, Page 5 (Wiley Periodicals, Inc. 2007). Accordingly, one skilled in the art would understand that the suture disclosed in the Frazier patent has a pore size that is at least less than approximately 200 microns. Thus, in summary, the Frazier patent seeks to take advantage of that microporosity to encourage the body's natural "foreign body response" of inflammation and scar tissue formation to create a fibrous scar about the suture.

GENERAL DESCRIPTION

In contrast, the present disclosure is directed to sutures designed to discourage that "foreign body response" of inflammation and fibrotic tissue formation about the suture by utilizing a macroporous structure. The macroporous structure seeks to minimize the foreign body response to the suture. In direct contrast to the microporous structure, the macroporous structure is optimized to achieve maximal biocompatibility by permitting neovascularization and local/normal tissue ingrowth into the suture itself.

In some embodiments, the present disclosure provides surgical sutures comprising a cross-sectional profile lacking radial symmetry. In some embodiments, the surgical suture comprises a ribbon-like geometry. In some embodiments, the suture is between 0.1 mm and 1 cm wide (e.g. >0.1 mm, >0.2 mm, >0.3 mm, >0.4 mm, >0.5 mm, >0.6 mm, >0.7 mm, >0.8 mm, >0.9 mm, >1 mm, >2 mm, >3 mm, >4 mm, >5 mm, >6 mm, >7 mm, >8 mm, >9 mm), although other dimensions may be used. In some embodiments, the suture is about 3.75 mm wide (e.g., 3 mm, 3.1 mm, 3.2 mm, 3.3 mm, 3.4 mm, 3.5 mm, 3.6 mm, 3.7 mm, 3.8 mm, 3.9 mm, 4.0 mm, 4.1 mm, 4.2 mm, 4.3 mm, 4.4 mm, 4.5 mm). In some embodiments, the suture comprises a 2D cross-sectional profile. In some embodiments, the 2D cross-sectional profile comprises an ellipse, half ellipse, gibbous, half circle, crescent, concave ribbon, or rectangle; although other shapes may be used. In some embodiments, the suture comprises polyethylene terephthalate, nylon, polyolefin, polypropylene, silk, polymers p-dioxanone, co-polymer of p-dioxanone, ε-caprolactone, glycolide, L(−)-lactide, D(+)-lactide, meso-lactide, trimethylene carbonate, polydioxanone homopolymer, and combinations thereof, although other materials may be used. In some embodiments, the suture comprises polypropylene. In some embodiments, a suture is sterile, surgical grade, medical grade, etc.

In some embodiments, the present disclosure provides surgical sutures comprising a flexible material containing one or more internal voids (e.g., hollow core, honeycomb, single or multiple lumen, etc.) that extend the length of the suture. In some embodiments, the surgical suture adopts a first cross-sectional profile in the absence of lateral stress, and a second cross-sectional profile in the presence of lateral stress. In some embodiments, the first cross-sectional profile exhibits substantial radial symmetry. In some embodiments, the second cross-sectional profile exhibits partially or wholly collapsed conformation.

In some embodiments, the present disclosure provides surgical sutures comprising material and structure configured to permit tissue in-growth upon placement of the suture into the tissue of a subject. In some embodiments, the material comprises pores that permit tissue in-growth. In some embodiments, the pores comprise macropores (e.g., pores having a diameter >200 µm, >300 µm, >400 µm, >500 µm, >600 µm, >700 µm, >800 µm, >900 µm, >1 mm, >2 mm, or more). In some embodiments, the pores comprise micropores (e.g., pores having a diameter <200 µm, <150 µm, <100 µm, <75 µm, <70 µm, <50 µm, <25 µm, <10 µm, <1 µm, <0.5 µm, <0.1 µm, or less). In some embodiment, the pores can include a combination of macropores and micropores. In some embodiments, the pores may be of any suitable shape (e.g., circular, diamond, amorphous, etc. In some embodiments, the material comprises a textured surface (e.g., grooves, web, mesh, ribs, barbs, etc.). In some embodiments, the suture comprises a cross-sectional profile lacking radial symmetry. In some embodiments, the suture comprises a cross-sectional profile lacking substantially radial symmetry. In some embodiments, the suture comprises a ribbon-like geometry. In some embodiments, the suture is between 1 mm and 1 cm wide. In some embodiments, the suture comprises a 2D cross-sectional profile. In some embodiments, the 2D cross-sectional profile comprises an ellipse, half ellipse, gibbous, half circle, crescent, concave ribbon, or rectangle. In some embodiments, the suture comprises polypropylene. In some embodiments, a suture is sterile, surgical grade, medical grade, etc.

In some embodiments, the present disclosure provides suturing needles comprising a distal end and a proximal end, wherein the proximal end is configured for attachment to a suture material, wherein the distal end in configured for insertion into tissue, and wherein the needle transitions from a radially symmetric cross-sectional profile (or substantially radially symmetric) or so-called triangular "cutting" configurations at the distal end to a cross-sectional profile lacking radial symmetry at the proximal end. In some embodiments, the needle produces a puncture lacking radial symmetry when inserted through a tissue. In some embodiments, the cross-sectional profile lacking radial symmetry comprises a ribbon-like geometry. In some embodiments, the ribbon-like geometry is between 1 mm and 1 cm wide. In some embodiments, the cross-sectional profile lacking radial symmetry comprises a 2D cross-sectional profile. In some embodiments, the 2D cross-sectional profile comprises an ellipse, half ellipse, gibbous, half circle, crescent, concave ribbon, or rectangle. In some embodiments, a suturing needle is sterile, surgical grade, medical grade, etc.

In some embodiments, the present disclosure comprises a suturing system comprising: (a) a suturing needle (e.g., as described above), comprising a distal end and a proximal end, wherein the proximal end is configured for attachment to a suture material, wherein the distal end is configured for insertion into tissue, and wherein the needle comprises a cross-sectional profile lacking radial symmetry at the proximal end of the needle; and (b) a surgical suture (e.g., as described above) comprising a cross-sectional profile lacking radial symmetry.

In some embodiments, the present disclosure provides methods of using any of the above sutures, suturing needles, and/or systems to suture a tissue and/or close an opening in a tissue (e.g., epidermal tissue, peritoneum, adipose tissue, cardiac tissue, or any other tissue in need of suturing).

In some embodiments, the present disclosure provides methods of suturing an opening in a tissue comprising: (a) providing a suture with distal and proximal ends, wherein said proximal end is attached to a needle, and wherein said distal end comprises an integrated loop structure; (b) inserting said needle through said tissue adjacent to a first end of said opening; (c) pulling said suture through said tissue until said distal end of said suture is adjacent to said tissue; (d) placing said needle and said suture through said loop to create a lasso at the distal end of said suture; (e) suturing closed said opening from said first end to a second end; (f) stapling said suture at a second end; and (g) cutting remaining suture material and needle proximal to the staple.

DETAILED DESCRIPTION

Figure 1:
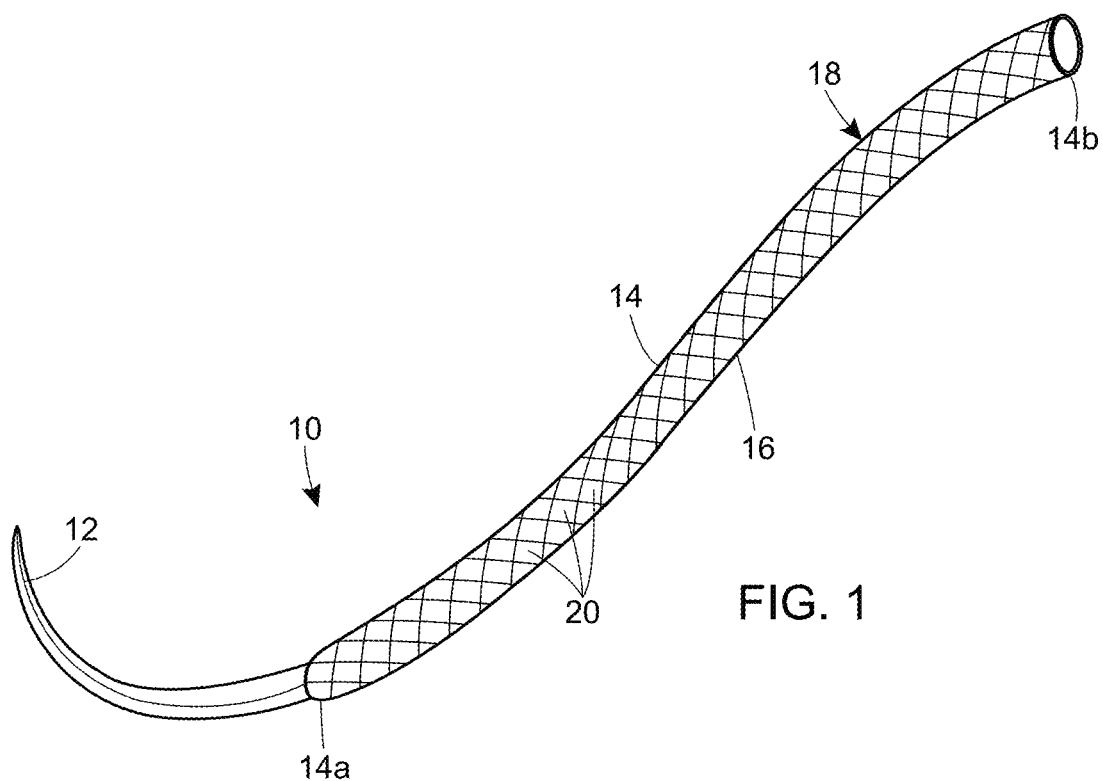
FIG. 1 shows an illustration of an exemplary integrated needle and suture comprising: (1) a sharp needle point, (2) needle body, (3) transition area, (4) flattened profile, (5) porous suture wall, and (6) hollow core.

The present disclosure provides a medical suture having a macroporous tubular construct that advantageously promotes neovascularization and normal tissue in-growth and integration subsequent to introduction into the body. Additionally, the present disclosure provides various sutures with increased surface area and/or tissue integrative properties and methods of use and manufacture thereof. In particular, provided herein are sutures with cross-section profiles and other structural characteristics that strengthen closure, prevent suture pull-through, and/or resist infection, and methods of use thereof. In some embodiments, sutures are provided that strengthen closure, prevent suture pull-through, and/or resist infection by, for example: (1) having a cross sectional profile that reduces pressure at suture points, (2) having a structural composition that allows tissue in-growth into the suture, or both (1) and (2). The present disclosure is not limited by any specific means for achieving the desired ends.

In some embodiments, conventional sutures exhibit a cross-sectional profile with radial symmetry or substantially radial symmetry. As used herein, the term "substantially radial symmetry" refers to a shape (e.g., cross-sectional profile) that approximates radial symmetry. A shape that has dimensions that are within 10% error of a shape exhibiting precise radial symmetry is substantially radially symmetric. For example, an oval that is 1.1 mm high and 1.0 mm wide is substantially radially symmetric. In some embodiments, the present disclosure provides sutures that lack radial symmetry and/or substantial radial symmetry.

In some embodiments, sutures are provided comprising cross-section shapes (e.g. flat, elliptical, etc.) that reduce tension against the tissue at the puncture site and reduce the likelihood of tissue tear. In some embodiments, devices (e.g., sutures) and methods provided herein reduce suture stress concentration at suture puncture points. In some embodiments, sutures with shaped cross-sectional profiles distribute forces more evenly (e.g., to the inner surface of the suture puncture hole) than traditional suture shapes/confirmation. In some embodiments, cross-sectionally-shaped sutures distribute tension about the suture puncture points. In some embodiments, rather than presenting a sharp point or line of suture to tissue, as is the case with traditional sutures, the sutures described herein present a flat or gently rounded plane to the leading edge of tissue, thereby increasing the surface area over which force can be distributed. In some embodiments, one cross-sectional dimension of the suture is greater than the orthogonal cross-sectional dimension (e.g., 1.1× greater, 1.2× greater, 1.3× greater, 1.4× greater, 1.5× greater, 1.6× greater, 1.7× greater, 1.8× greater, 1.9× greater, >2× greater, 2.0× greater, 2.1× greater, 2.2× greater, 2.3× greater, 2.4× greater, 2.5× greater, 2.6× greater, 2.7× greater, 2.8× greater, 2.9× greater, 3.0× greater, >3.0× greater, 3.1× greater, 3.2× greater, 3.3× greater, 3.4× greater, 3.5× greater, 3.6× greater, 3.7× greater, 3.8× greater, 3.9× greater, 4.0× greater, >4.0× greater . . . >5.0× greater . . . >6.0× greater . . . >7.0× greater . . . >8.0× greater . . . >9.0× greater . . . >10.0× greater). In some embodiments, sutures provided herein are flat or ellipsoidal on cross section, forming a ribbon-like conformation. In some embodiments, sutures are provided that do not present a sharp leading edge to the tissue. In some embodiments, use of the sutures described herein reduces the rates of surgical dehiscence in all tissues (e.g., hernia repairs, etc.). In some embodiments, sutures are provided with cross-sectional profiles that provide optimal levels of strength, flexibility, compliance, macroporosity, and/or durability while decreasing the likelihood of suture pull-through. In some embodiments, sutures are provided with sizes or shapes to enlarge the suture/tissue interface of each suture/tissue contact point, thereby distributing force over a greater area.

In some embodiments, sutures of the present disclosure provide various improvements over conventional sutures. In some embodiments, sutures provide: reduced likelihood of suture pull-through, increased closure strength, decreased number of stitches for a closure, more rapid healing times, and/or reduction in closure failure relative to a traditional suture. In some embodiments, relative improvements in suture performance (e.g., initial closure strength, rate of achieving tissue strength, final closure strength, rate of infection, etc.) are assessed in a tissue test model, animal test model, simulated test model, in silico testing, etc. In some embodiments, sutures of the present disclosure provide increased initial closure strength (e.g., at least a 10% increase in initial closure strength (e.g., >10%, >25%, >50%, >75%, >2-fold, >3-fold, >4-fold, >5-fold, >10-fold, or more). As used herein, "initial closure strength" refers to the strength of the closure (e.g., resistance to opening), prior to strengthening of the closure by the healing or scarring processes. In some embodiments, the increased initial closure strength is due to mechanical distribution of forces across a larger load-bearing surface area that reduces micromotion and susceptibility to pull through. In some embodiments, sutures of the present disclosure provide increased rate of achieving tissue strength (e.g., from healing of tissue across the opening, from ingrowth of tissue into the integrative (porous) design of the suture, etc.). In some embodiments, sutures of the present disclosure provide at least a 10% increase in rate of achieving tissue strength (e.g., >10%, >25%, >50%, >75%, >2-fold, >3-fold, >4-fold, >5-fold, >10-fold, or more). In some embodiments, increased rate of return of tissue strength across the opening further increases load bearing surface area, thereby promoting tissue stability and decreased susceptibility to pull through. In some embodiments, sutures of the present disclosure establish closure strength earlier in the healing process (e.g., due to greater initial closure strength and/or greater rate of achieving tissue strength) when the closure is most susceptible to rupture (e.g., at least a 10% reduction in time to establish closure strength (e.g., >10% reduction, >25% reduction, >50% reduction, >75% reduction, >2-fold reduction, >3-fold reduction, >4-fold reduction, >5-fold reduction, >10-fold reduction, or more)). In some embodiments, sutures of the present disclosure provide increased final closure strength (e.g., at least a 10% increase in final closure strength (e.g., >10%, >25%, >50%, >75%, >2-fold, >3-fold, >4-fold, >5-fold, >10-fold, or more). In some embodiments, the strength of fully healed closure is created not only by interface between the two apposed tissue surfaces, as is the case with conventional suture closures, but also along the total surface area of the integrated suture. In some embodiments, tissue integration into the suture decreases the rate of suture abscesses and/or infections that otherwise occur with solid foreign materials of the same size (e.g., at least a 10% reduction in suture abscesses and/or infection (e.g., >10% reduction, >25% reduction, >50% reduction, >75% reduction, >2-fold reduction, >3-fold reduction, >4-fold reduction, >5-fold reduction, >10-fold reduction, or more)). In some embodiments, sutures provide at least a 10% reduction (e.g., >10%, >20%, >30%, >40%, >50%, >60%, >70%, >80%, >90%, or more) in suture pull-through (e.g. through tissue (e.g., epidermal tissue, peritoneum, adipose tissue, cardiac tissue, or any other tissue in need of suturing), or through control substance (e.g., ballistic gel)).

In some embodiments, sutures are provided with any suitable cross-section profile or shape that provides reduced stress at the tissue puncture site, point of contact with tissue, and/or closure site. In some embodiments, sutures have cross-sectional dimensions (e.g., width and/or depth) or between 0.1 mm and 1 cm (e.g., 0.1 mm . . . 0.2 mm . . . 0.5 mm . . . 1.0 mm . . . 2.0 mm . . . 5.0 mm . . . 1 cm). In some embodiments, the suture dimensions (e.g., width and/or depth) that minimize pull-through and/or provide maximum load are utilized. In some embodiments, optimal suture dimensions are empirically determined for a given tissue and suture material. In some embodiments, one or both cross-sectional dimensions of a suture are the same as the cross-sectional dimensions of a traditional suture. In some embodiments, a suture comprises the same cross-sectional area as a traditional suture, but with different shape and/or dimensions. In some embodiments, a suture comprises the greater cross-sectional area than a traditional suture. In some embodiments, a suture cross-section provides a broad leading edge to spread pressure out over a broader portion of tissue. In some embodiments, a suture cross-section provides a shaped leading edge (e.g., convex) that evenly distributes force along a segment of tissue, rather than focusing it at a single point. In some embodiments, shaped sutures prevent pull-through by distributing forces across the tissue rather than focusing them at a single point. In some embodiments, sutures prevent pull-through by providing a broader cross-section that is more difficult to pull through tissue.

In some embodiments, ribbon-like suture or flat sutures are provided. In some embodiments, sutures provided herein comprise any suitable cross-sectional shape that provides the desired qualities and characteristics. In some embodiments, suture cross-sectional shape provides enhanced and/or enlarged leading edge surface distance and/or area (e.g. to reduce localized pressure on tissue). In some embodiments, suture cross-sectional shape comprises: an ellipse, half-ellipse, half-circle, gibbous, rectangle, square, crescent, pentagon, hexagon, concave ribbon, convex ribbon, H-beam, I-beam, dumbbell, etc. In some embodiments, a suture cross-sectional profile comprises any combination of curves, lines, corners, bends, etc. to achieve a desired shape. In some embodiments, the edge of the sutures configured to contact the tissue and/or place pressure against the tissue is broader than one or more other suture dimensions. In some embodiments, the edge of the sutures configured to contact the tissue and/or place pressure against the tissue is shaped to evenly distribute forces across the region of contact.

In some embodiments, hollow core sutures are provided such as that depicted in FIG. 1. More specifically, FIG. 1 depicts a medical device 10 that includes a surgical needle 12 and an elongated suture 14. In FIG. 1, the needle 12 includes a contoured or curved needle with a flattened cross-sectional profile, but needles with generally any geometry could be used. The suture 14 can be a hollow core suture with a first end 14a attached to the needle 12 and a second end 14b located a distance away from the needle 12. As shown, the entire length of the suture 14 between the first and second ends 14a, 14b can include a tubular wall 16 that defines a hollow core 18. In other versions, however, less than the entire length of the suture 14 can be tubular. For example, it is foreseeable that either or both of the first and second ends 14a, 14b can have a non-tubular portion or portion of other geometry. Such non-tubular portions could be for attaching the first end 14a of the suture 14 to the needle 12 or for tying off the second end 14b, for example. In versions where the entire length of the suture 14 is tubular, as shown, the entire length of the suture 14 including the ends and central portion also has generally a constant or uniform diameter or thickness in the absence of stresses. That is, no portion of the suture 14 is meaningfully larger in diameter than any other portion of the suture 14. Moreover, no aspect, end, or other portion of the suture 14 is intended to be or is actually passed through, disposed in, received in, or otherwise positioned inside of the hollow core 18. The hollow core 18 is adapted for receiving tissue in-growth only.

In some embodiments, the tubular wall 16 can have a diameter in a range of approximately 1 mm to approximately 10 mm and can be constructed of a material such as, for example, polyethylene terephthalate, nylon, polyolefin, polypropylene, silk, polymers p-dioxanone, co-polymer of p-dioxanone, ε-caprolactone, glycolide, L(−)-lactide, D(+)-lactide, meso-lactide, trimethylene carbonate, polydioxanone homopolymer, and combinations thereof. So constructed, the tubular wall 16 of the suture 14 can be radially deformable such that it adopts a first cross-sectional profile in the absence of lateral stresses and a second cross-sectional profile in the presence of lateral stresses. For example, in the absence of lateral stresses, the tubular wall 16 and therefore the suture 14 depicted in FIG. 1, for example, can have a circular cross-sectional profile, thereby exhibiting radial symmetry. In the presence of a lateral stress, such a suture 14 could then exhibit a partially or wholly collapsed conformation.

In at least one version of the medical device 10, at least some of the tubular wall 16 can be macroporous defining a plurality of pores 20 (e.g., openings, apertures, holes, etc.), only a few of which are expressly identified by reference number and lead line in FIG. 1 for clarity. The pores 20 extend completely through the mesh wall 16 to the hollow core 18. In some versions, the tubular wall 16 can be constructed of a woven or knitted mesh material. In one version, the wall 16 can be constructed of a knitted polypropylene mesh material similar or identical to that which is available under the trade name Prolene Soft Mesh and offered for sale by Ethicon. Other similarly constructed mesh materials would be suitable as well.

Figure 1A:
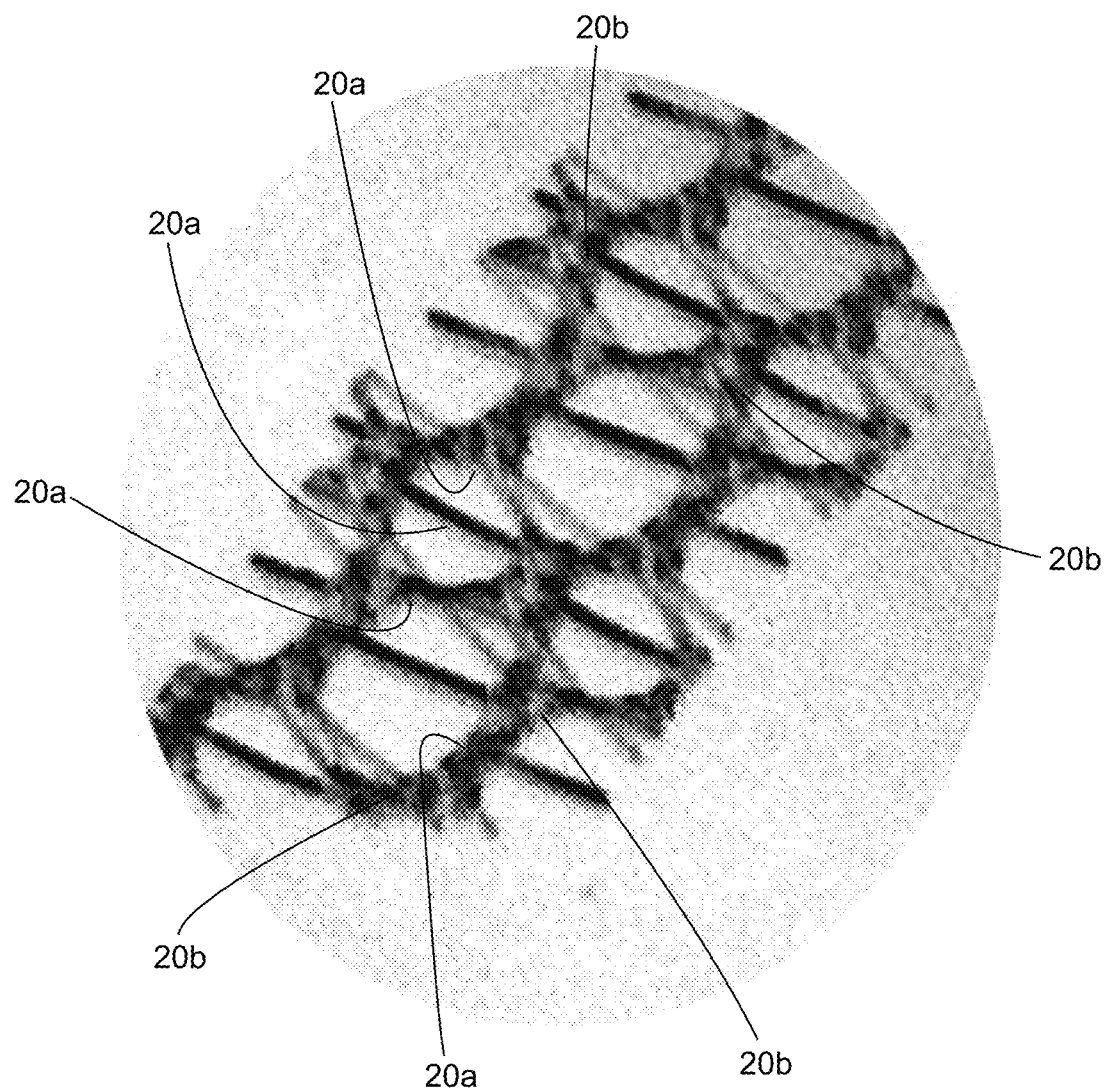
FIG. 1A is a detailed view of a portion of the porous suture wall of FIG. 1.

As used herein, the term "macroporous" can include pore sizes that are at least greater than or equal to approximately 200 microns and, preferably, greater than or equal to 500 microns. In some versions of the medical device 10, the size of at least some the pores 20 in the suture 14 can be in a range of approximately 500 microns to approximately 4 millimeters. In another version, at least some of the pores 20 can have a pore size in the range of approximately 500 microns to approximately 2.5 millimeters. In another version, at least some of the pores 20 can have a pore size in the range of approximately 1 millimeter to approximately 2.5 millimeters. In another version, the size of at least some of the pores 20 can be approximately 2 millimeters. Moreover, in some versions, the pores 20 can vary in size. For example, as mentioned above and as also illustrated in FIG. 1A, in some versions, some of the pores 20a can be macroporous (e.g., greater than approximately 200 microns) and some of the pores 20b can be microporous (e.g., less than approximately 200 microns). The presence of microporosity (i.e., pores less than approximately 200 microns) in such versions of the disclosed suture may only be incidental to the manufacturing process, which can including knitting, weaving, extruding, blow molding, or otherwise, but not necessarily intended for any other functional reason regarding biocompatibility or tissue integration. The presence of microporosity (i.e, some pores less than approximately 200 microns in size) as a byproduct or incidental result of manufacturing does not change the character of the disclosed macroporous suture (e.g., with pores greater than approximately 200 microns, and preferably greater than approximately 500 microns, for example), which facilitates tissue in-growth to aid biocompatibility, reduce tissue inflammation, and decrease suture pull-through.

In versions of the disclosed suture that has both macroporosity and microporosity, the number of pores 20 that are macroporous can be in a range from approximately 1% of the pores to approximately 99% of the pores (when measured by pore cross-sectional area), in a range from approximately 5% of the pores to approximately 99% of the pores (when measured by pore cross-sectional area), in a range from approximately 10% of the pores to approximately 99% of the pores (when measured by pore cross-sectional area), in a range from approximately 20% of the pores to approximately 99% of the pores (when measured by pore cross-sectional area), in a range from approximately 30% of the pores to approximately 99% of the pores (when measured by pore cross-sectional area), in a range from approximately 50% of the pores to approximately 99% of the pores (when measured by pore cross-sectional area), in a range from approximately 60% of the pores to approximately 99% of the pores (when measured by pore cross-sectional area), in a range from approximately 70% of the pores to approximately 99% of the pores (when measured by pore cross-sectional area), in a range from approximately 80% of the pores to approximately 99% of the pores (when measured by pore cross-sectional area), or in a range from approximately 90% of the pores to approximately 99% of the pores (when measured by pore cross-sectional area).

So configured, the pores 20 in the suture 14 are arranged and configured such that the suture 14 is adapted to facilitate and allow tissue in-growth and integration through the pores 20 in the mesh wall 16 and into the hollow core 18 when introduced into a body. That is, the pores 20 are of sufficient size to achieve maximum biocompatibility by promoting neovascularization and local/normal tissue in-growth through the pores 20 and into the hollow core 18 of the suture 14. As such, tissue growth through the pores 16 and into the hollow core 20 enables the suture 14 and resultant tissue to combine and cooperatively increase the strength and efficacy of the medical device 10, while also decreasing irritation, inflammation, local tissue necrosis, and likelihood of pull through. Instead, the suture 14 promotes the production of healthy new tissue throughout the suture construct including inside the pores 20 and the hollow core 18.

Figure 5:
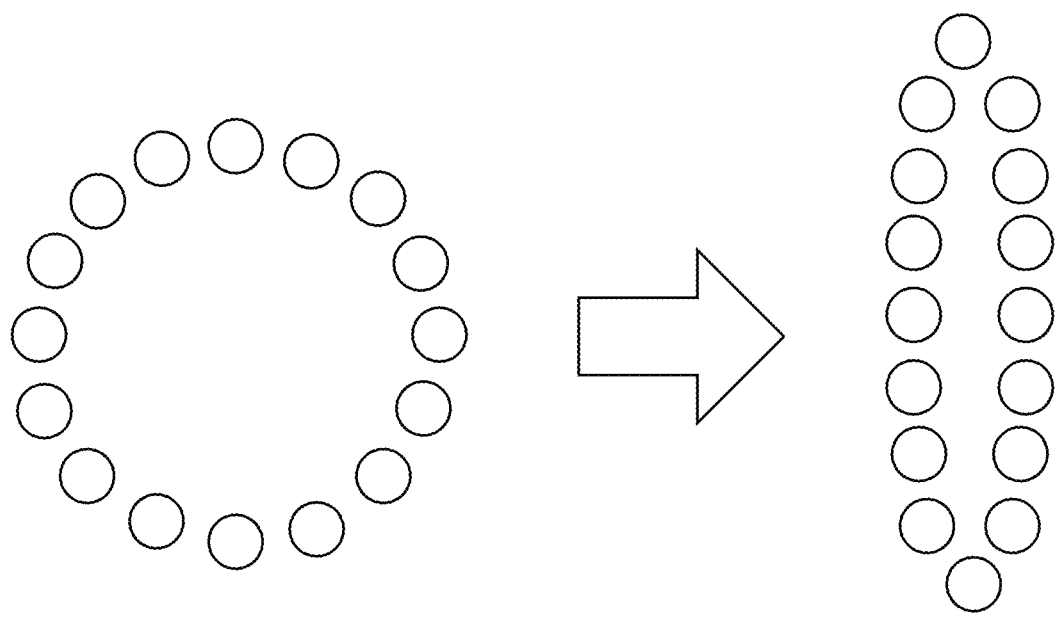
FIG. 5 shows a schematic demonstrating an altered cross-sectional profile upon application of non-axial force to a hollow core suture.

While the suture 14 in FIG. 1 has been described as including a single elongated hollow core 18, in some embodiments, a suture according to the present disclosure can comprise a tubular wall defining a hollow core including one or more interior voids (e.g., extending the length of the suture). In some versions, at least some of the interior voids can have a size or diameter >approximately 200 microns, >approximately 300 microns, >approximately 400 microns, >approximately 500 microns, >approximately 600 microns, >approximately 700 microns, >approximately 800 microns, >approximately 900 microns, >approximately 1 millimeter, or >approximately 2 millimeters. In some embodiments, a suture according to the present disclosure can comprise a tubular wall defining a hollow core including one or more (e.g., 1, 2, 3, 4, 5, 6, 7, 8, or more) lumens (e.g., running the length of the suture). In some embodiments, a suture according to the present disclosure can comprise a tubular wall defining a hollow core including a honeycomb structure, a 3D lattice structure, or other suitable interior matrix, which defines one or more interior voids. In some versions, at least some of the interior voids in the honeycomb structure, 3D lattice structure, or other suitable matrix can have a size or diameter >approximately 200 microns, >approximately 300 microns, >approximately 400 microns, >approximately 500 microns, >approximately 600 microns, >approximately 700 microns, >approximately 800 microns, >approximately 900 microns, >approximately 1 millimeter, or >approximately 2 millimeters. In some embodiments, a void comprises a hollow core. In some embodiments, a hollow core can include a hollow cylindrical space in the tubular wall, but as described, the term "hollow core" is not limited to defining a cylindrical space, but rather could include a labyrinth of interior voids defined by a honeycomb structure, a 3D lattice structure, or some other suitable matrix. In some embodiments, sutures comprise a hollow, flexible structure that has a circular cross-sectional profile in its non-stressed state, but which collapses into a more flattened cross-sectional shape when pulled in an off-axis direction. In some embodiments, sutures are provided that exhibit radial symmetry in a non-stressed state. In some embodiments, radial symmetry in a non-stressed state eliminates the need for directional orientation while suturing. In some embodiments, sutures are provided that exhibit a flattened cross-sectional profile when off-axis (longitudinal axis) force is applied (e.g., tightening of the suture against tissue) (SEE FIG. 5), thereby more evenly distributing the force applied by the suture on the tissue. In some embodiments, sutures are provided that exhibit a flattened cross-sectional profile when axial force is applied. In some embodiments, sutures comprise flexible structure that adopts a first cross-sectional profile in its non-stressed state (e.g., suturing profile), but adopts a second cross-sectional shape when pulled in an off-axis direction (e.g., tightened profile). In some embodiments, a suture is hollow and/or comprises one or more internal voids (e.g., that run the length of the suture). In some embodiments, internal voids are configured to encourage the suture to adopt a preferred conformation (e.g., broadened leading edge to displace pressures across the contacted tissue) when in a stressed states (e.g., tightened profile). In some embodiments, internal voids are configured to allow a suture to adopt radial exterior symmetry (e.g., circular outer cross-sectional profile) when in a non-stressed state. In some embodiments, varying the size, shape, and/or placement of internal voids alters one or both of the first cross-sectional profile (e.g., non-stressed profile, suturing profile) and second cross-sectional profile (e.g., off-axis profile, stressed profile, tightened profile).

Figure 2:
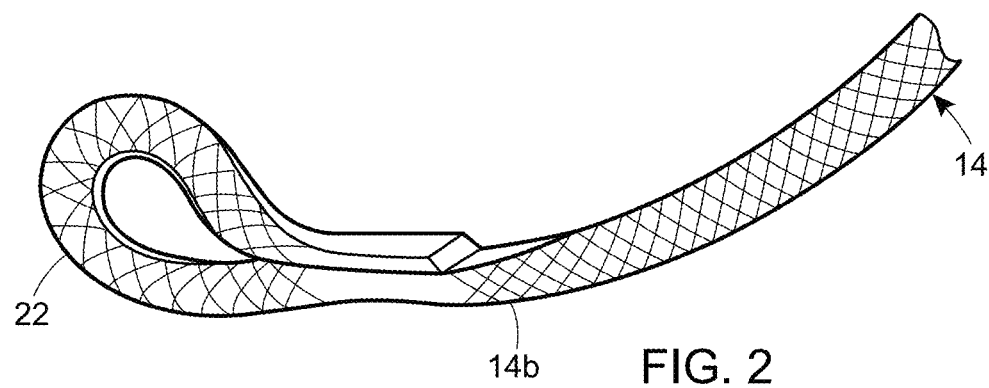
FIG. 2 shows an illustration of an exemplary anchor end comprising a crimped loop: (1) crimpled joint, (2) circular profile.
Figure 3:
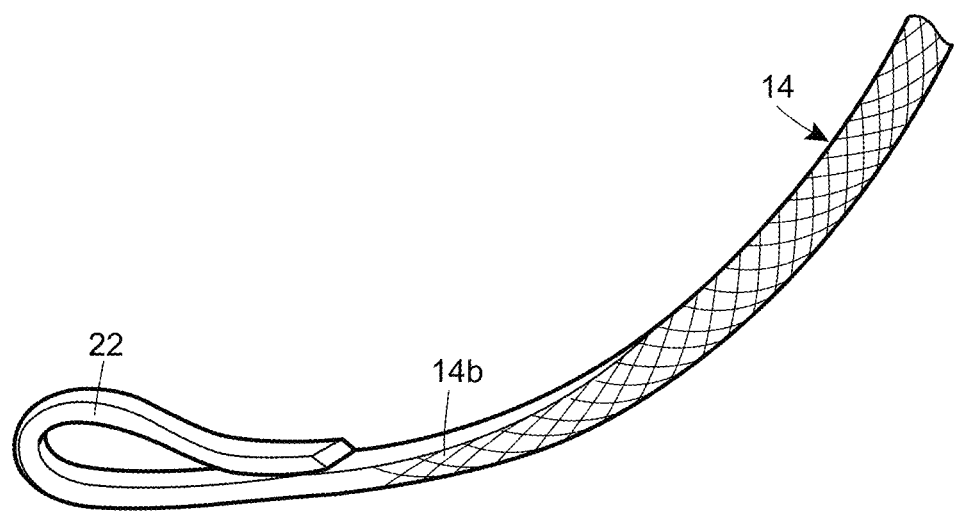
FIG. 3 shows an illustration of an exemplary anchor end comprising a flattened loop: (1) flattened loop, (2) transition area, (3) circular profile.
Figure 4:
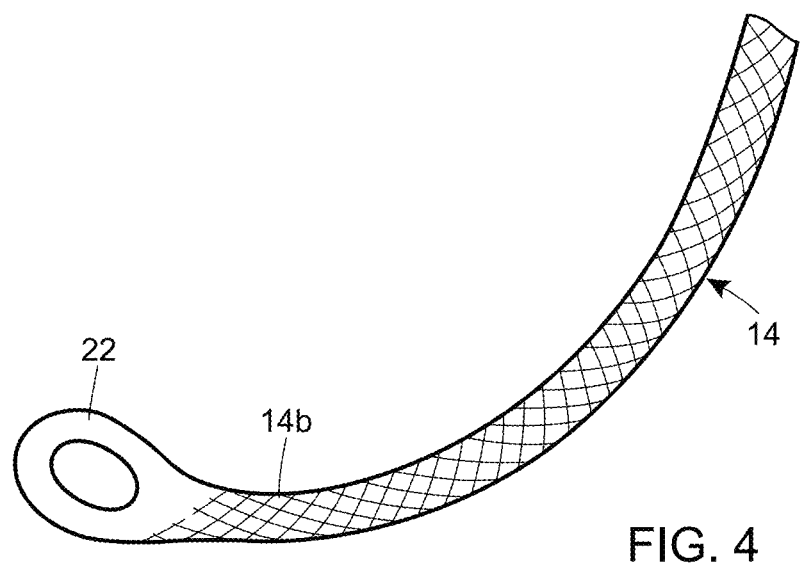
FIG. 4 shows an illustration of an exemplary anchor end comprising a formed loop: (1) formed joint, (2) circular profile.

Sutures, which are substantially linear in geometry, have two distinct ends, as described above with reference to FIG. 1, for example. In some embodiments, both ends are identical. In some embodiments, each end is different. In some embodiments, one or both ends are structurally unadorned. In some embodiments, one or more ends is attached to or at least configured for attachment to a needle via swaging, sonic welding, adhesive, tying, or some other means (as shown FIG. 1). In some embodiments, the second end 14b of the suture 14 is configured to include an anchor 22 (e.g., FIGS. 2, 3 and 4) for anchoring the suture 14 against the tissue through which the suture 14 is inserted. In some embodiments, the second end 14b of the suture 14 is configured to anchor the suture at the beginning of the closure. In some embodiments, the second end 14b of the suture 14 includes an anchor 22 that is a structure that prevents the suture 14 from being pulled completely through the tissue. In some embodiments, the anchor 22 has a greater dimension than the rest of the suture 14 (at least 10% greater, at least 25% greater, at least 50% greater, at least 2-fold greater, at least 3-fold greater, at least 4-fold greater, at least 5-fold greater, at least 6-fold greater, at least 10-fold greater, etc.). In some embodiments, the anchor 22 comprises a structure with any suitable shape for preventing the suture 14 from being pulled through the hole (e.g., ball, disc, plate, cylinder), thereby preventing the suture 14 from being pulled through the insertion hole. In some embodiments, the anchor 22 of the suture 14 comprises a closed loop, as depicted in FIG. 2, for example. In some embodiments, the closed loop is of any suitable structure including, but not limited to a crimpled loop (FIG. 2), flattened loop (FIG. 3), or a formed loop (FIG. 4). In some embodiments, a loop can be integrated into the end of the suture 14. In some embodiments, a separate loop structure can be attached to the suture 14. In some embodiments, the needle 12 can be passed through the closed loop anchor 22 to create a cinch for anchoring the suture 14 to that point. In some embodiments, the anchor 22 can comprise one or more structures (e.g., barb, hook, etc.) to hold the end of the suture 14 in place. In some embodiments, one or more anchor 22 structures (e.g., barb, hook, etc.) are used in conjunction with a closed loop to ratchet down the cinch and hold its position. In some embodiments, a knotless anchoring system can be provided.

In some embodiments, and as briefly mentioned relative to FIG. 1, the present disclosure provides suturing needles with cross-sectional profiles configured to prevent suture pull-through and methods of use thereof. In some embodiments, suturing needles are provided comprising cross-section shapes (e.g. flat, elliptical, transitioning over the length of the needle, etc.) that reduce tension against the tissue at the puncture site and reduce the likelihood of tissue tear. In some embodiments, one cross-sectional dimension of the needle is greater than the orthogonal cross-sectional dimension (e.g., 1.1× greater, 1.2× greater, 1.3× greater, 1.4× greater, 1.5× greater, 1.6× greater, 1.7× greater, 1.8× greater, 1.9× greater, >2× greater, 2.0× greater, 2.1× greater, 2.2× greater, 2.3× greater, 2.4× greater, 2.5× greater, 2.6× greater, 2.7× greater, 2.8× greater, 2.9× greater, 3.0× greater, >3.0× greater, 3.1× greater, 3.2× greater, 3.3× greater, 3.4× greater, 3.5× greater, 3.6× greater, 3.7× greater, 3.8× greater, 3.9× greater, 4.0× greater, >4.0× greater . . . >5.0× greater . . . >6.0× greater . . . >7.0× greater . . . >8.0× greater . . . >9.0× greater . . . >10.0× greater). In some embodiments, suturing needles are provided circular in shape at its point (e.g., distal end), but transition to a flattened profile (e.g., ribbon-like) to the rear (e.g. proximal end). In some embodiments, the face of the flattened area is orthogonal to the radius of curvature of the needle. In some embodiments, suturing needles create a slit (or flat puncture) in the tissue as it is passed through, rather than a circle or point puncture. In some embodiments, suturing needles are provided circular in shape at its point (e.g., distal end), but transition to a 2D cross-sectional profile (e.g., ellipse, crescent, half moon, gibbous, etc.) to the rear (e.g. proximal end). In some embodiments, suturing needles provided herein find use with the sutures described herein. In some embodiments, suturing needles find use with sutures of the same shape and/or size. In some embodiments, suturing needles and sutures are not of the same size and/or shape. In some embodiments, suturing needles provided herein find use with traditional sutures. Various types of suture needles are well known in the art. In some embodiments, suturing needles provided herein comprise any suitable characteristics of suturing needles known to the field, but modified with dimensions described herein.

In some embodiments, the present disclosure also provides compositions, methods, and devices for anchoring the suture at the end of the closure (e.g., without tying the suture to itself). In some embodiments, one or more securing elements (e.g., staples) are positioned over the terminal end of the suture to secure the end of the closure. In some embodiments, one or more securing elements (e.g., staples) are secured to the last "rung" of the suture closure (e.g., to hold the suture tight across the closure. In some embodiments, a securing element is a staple. In some embodiments, a staple comprises stainless steel or any other suitable material. In some embodiments, a staple comprises a plurality of pins that can pass full thickness through 2 layers of suture. In some embodiments, staple pins are configured to secure the suture end without cutting and/or weakening the suture filament. In some embodiments, a staple forms a strong joint with the suture. In some embodiments, a staple is delivered after the needle is cut from the suture. In some embodiments, a staple is delivered and the needle removed simultaneously In some embodiments, the present disclosure provides devices (e.g., staple guns) for delivery of a staple into tissue to secure the suture end. In some embodiments, a staple deployment device simultaneously or near-simultaneously delivers a staple and removes the needle from the suture. In some embodiments, a staple deployment device comprises a bottom lip or shelf to pass under the last rung of suture (e.g., between the suture and tissue surface) against which the pins of the staple can be deformed into their locked position. In some embodiments, the bottom lip of the staple deployment device is placed under the last rung of suture, the free tail of the suture is placed within the stapling mechanism, and the suture is pulled tight. In some embodiments, while holding tension, the staple deployment device is activated, thereby joining the two layers of suture together. In some embodiments, the device also cuts off the excess length of the free suture tail. In some embodiments, the staple deployment device completes the running suture and trims the excess suture in one step. In some embodiments, a suture is secured without the need for knot tying. In some embodiments, only 1 staple is needed per closure. In some embodiments, a standard stapler is used to apply staples and secure the suture end. In some embodiments, a staple is applied to the suture end manually.

In some embodiments, sutures provided herein provide tissue integrative properties to increase the overall strength of the repair (e.g., at an earlier time-point than traditional sutures). In some embodiments, sutures are provided with enhanced tissue adhesion properties. In some embodiments sutures are provided that integrate with the surrounding tissue. In some embodiments, tissue integrative properties find use in conjunction with any other suture characteristics described herein. In some embodiments, sutures allow integration of healing tissue into the suture. In some embodiments, tissue growth into the suture is promoted (e.g., by the surface texture of the suture). In some embodiments, tissue growth into the suture prevents sliding of tissue around suture, and/or minimizes micromotion between suture and tissue. In some embodiments, tissue in-growth into the suture increases the overall strength of the repair by multiplying the surface area for scar in establishing continuity between tissues. Conventionally, the strength of a repair is dependent only on the interface between the two tissue surfaces being approximated. In some embodiments ingrowth of tissue into the suture adds to the surface area of the repair, thereby enhancing its strength. In some embodiments, increasing the surface area for scar formation, the closure reaches significant strength more quickly, narrowing the window of significant risk of dehiscence.

In some embodiments, the surface and/or internal texture of a suture promote tissue adhesion and/or ingrowth. In some embodiments, as discussed above specifically with reference to FIG. 1, a suture of the present disclosure can comprise a porous (e.g., macroporous) and/or textured material. In some embodiments, a suture comprises a porous (e.g., macroporous) and/or textured exterior. In some embodiments, pores in the suture allow tissue in-growth and/or integration. In some embodiments, a suture comprises a porous ribbon-like structure, instead of a tubular like structure. In some embodiments, a porous suture comprises a 2D cross-sectional profile (e.g., elliptical, circular (e.g., collapsible circle), half moon, crescent, concave ribbon, etc.). In some embodiments, a porous suture comprises polypropylene or any other suitable suture material. In some embodiments, pores are between 500 µm and 3.5 mm or greater in diameter (e.g., e.g., >500 µm in diameter (e.g., >500 µm, >600 µm, >700 µm, 800 µm, >900 µm, >1 mm, or more). In some embodiments pores are of varying sizes. In some embodiments, a suture comprises any surface texture suitable to promote tissue in-growth and/or adhesion. In some embodiments, suitable surface textures include, but are not limited to ribbing, webbing, mesh, grooves, etc. In some embodiments, the suture may include filaments or other structures (e.g., to provide increased surface area and/or increased stability of suture within tissue). In some embodiments, interconnected porous architecture is provided, in which pore size, porosity, pore shape and/or pore alignment facilitates tissue in-growth.

In some embodiments, a suture comprises a mesh and/or mesh-like exterior. In some embodiments, a mesh exterior provides a flexible suture that spreads pressure across the closure site, and allows for significant tissue in-growth. In some embodiments, the density of the mesh is tailored to obtain desired flexibility, elasticity, and in-growth characteristics.

In some embodiments, a suture is coated and/or embedded with materials to promote tissue ingrowth. Examples of biologically active compounds that may be used sutures to promote tissue ingrowth include, but are not limited to, cell attachment mediators, such as the peptide containing variations of the "RGD" integrin binding sequence known to affect cellular attachment, biologically active ligands, and substances that enhance or exclude particular varieties of cellular or tissue ingrowth. Such substances include, for example, osteoinductive substances, such as bone morphogenic proteins (BMP), epidermal growth factor (EGF), fibroblast growth factor (FGF), platelet-derived growth factor (PDGF), insulin-like growth factor (IGF-I and II), TGF-β, etc. Examples of pharmaceutically active compounds that may be used sutures to promote tissue ingrowth include, but are not limited to, acyclovir, cephradine, malfalen, procaine, ephedrine, adriomycin, daunomycin, plumbagin, atropine, guanine, digoxin, quinidine, biologically active peptides, chlorin e.sub.6, cephalothin, proline and proline analogues such as cis-hydroxy-L-proline, penicillin V, aspirin, ibuprofen, steroids, nicotinic acid, chemodeoxycholic acid, chlorambucil, and the like. Therapeutically effective dosages may be determined by either in vitro or in vivo methods.

Sutures are well known medical devices in the art. In some embodiments, sutures have braided or monofilament constructions. In some embodiments sutures are provided in single-armed or double-armed configurations with a surgical needle mounted to one or both ends of the suture, or may be provided without surgical needles mounted. In some embodiments, the end of the suture distal to the needle comprises one or more structures to anchor the suture. In some embodiments, the distal end of the suture comprises one or more of a: closed loop, open loop, anchor point, barb, hook, etc. In some embodiments, sutures comprise one or more biocompatible materials. In some embodiments, sutures comprise one or more of a variety of known bioabsorbable and nonabsorbable materials. For example, in some embodiments, sutures comprise one or more aromatic polyesters such as polyethylene terephthalate, nylons such as nylon 6 and nylon 66, polyolefins such as polypropylene, silk, and other nonabsorbable polymers. In some embodiments, sutures comprise one or more polymers and/or copolymers of p-dioxanone (also known as 1,4-dioxane-2-one), ε-caprolactone, glycolide, L(−)-lactide, D(+)-lactide, meso-lactide, trimethylene carbonate, and combinations thereof. In some embodiments, sutures comprise polydioxanone homopolymer. The above listing of suture materials should not be viewed as limiting. Suture materials and characteristics are known in the art. Any suitable suture materials or combinations thereof are within the scope of the present disclosure. In some embodiments, sutures comprise sterile, medical grade, surgical grade, and or biodegradable materials. In some embodiments, a suture is coated with, contains, and/or elutes one or more bioactive substances (e.g., antiseptic, antibiotic, anesthetic, promoter of healing, etc.).

In some embodiments, the structure and material of the suture provides physiologically-tuned elasticity. In some embodiments, a suture of appropriate elasticity is selected for a tissue. In some embodiments, suture elasticity is matched to a tissue. For example, in some embodiments, sutures for use in abdominal wall closure will have similar elasticity to the abdominal wall, so as to reversibly deform along with the abdominal wall, rather than act as a relatively rigid structure that would carry higher risk of pull-through. In some embodiments, elasticity would not be so great however, so as to form a loose closure that could easily be pulled apart. In some embodiments, deformation of the suture would start occurring just before the elastic limit of its surrounding tissue, e.g., before the tissue starts tearing or irreversibly deforming.

In some embodiments, sutures described herein provide a suitable replacement or alternative for surgical repair meshes (e.g., those used in hernia repair). In some embodiments, the use of sutures in place of mesh reduces the amount of foreign material placed into a subject (e.g., 50 cm$^2$ (suture) v. 240 cm$^2$ (mesh)). In some embodiments, the decreased likelihood of suture pull-through allows the use of sutures to close tissues not possible with traditional sutures (e.g., areas of poor tissue quality (e.g., friable or weak tissue) due to conditions like inflammation, fibrosis, atrophy, denervation, congenital disorders, attenuation due to age, or other acute and chronic diseases). Like a surgical mesh, sutures described herein permit a distribution of forces over a larger area thereby delocalizing forces felt by the tissue and reducing the chance of suture pull-though and failure of the closure.

In some embodiments, sutures are permanent, removable, or absorbable. In some embodiments, permanent sutures provide added strength to a closure or other region of the body, without the expectation that the sutures will be removed upon the tissue obtaining sufficient strength. In such embodiments, materials are selected that pose little risk of long-term residency in a tissue or body. In some embodiments, removable sutures are stable (e.g., do not readily degrade in a physiological environment), and are intended for removal when the surrounding tissue reaches full closure strength. In some embodiments, absorbable sutures integrate with the tissue in the same manner as permanent or removable sutures, but eventually (e.g., >1 week, >2 weeks, >3 weeks, >4 weeks, >10 weeks, >25 weeks, >1 year) biodegrade and/or are absorbed into the tissue after having served the utility of holding the tissue together during the postoperative and/or healing period. In some embodiments absorbable sutures present a reduced foreign body risk.

Although prevention of dehiscence of abdominal closures (e.g., hernia formation) is specifically described at an application of embodiments of the present disclosure, the sutures described herein are useful for joining any tissue types throughout the body. In some embodiments, sutures described herein are of particular utility to closures that are subject top tension and/or for which cheesewiring is a concern. Exemplary tissues within which the present disclosure finds use include, but are not limited to: connective tissue, muscle, dermal tissue, cartilage, tendon, or any other soft tissues. Specific applications of sutures described herein include placation, suspensions, slings, etc. Sutures described herein find use in surgical procedures, non-surgical medical procedures, veterinary procedures, in-field medical procedures, etc. The scope of the present disclosure is not limited by the potential applications of the sutures described herein.

Yet, from the foregoing, it should also be appreciated that the present disclosure additionally provides both a novel method of re-apposing soft tissue and a novel method of manufacturing a medical device.

Based on the present disclosure, a method of re-apposing soft tissue can first include piercing a portion of the soft tissue with the surgical needle 12 (as shown in FIG. 1, for example) attached to a first end 14a of a tubular suture 14. Next, a physician can thread the tubular suture 14 through the soft tissue and make one or more stitches, as is generally known. Finally, the physician can anchor the tubular suture 14 in place in the soft tissue. As disclosed hereinabove, the tubular suture 14 comprises a tubular mesh wall 16 defining a hollow core 18. The tubular mesh wall 16 defines a plurality or pores 20, each with a pore size that is greater than or equal to approximately 500 microns. So configured, the tubular suture 14 is adapted to accommodate the soft tissue growing through the tubular mesh wall 16 and into the hollow core 18, thereby integrating with the suture. In some versions, the method can further and finally include anchoring the tubular suture 14 in place by passing the surgical needle 12 through a closed loop anchor 22 (as seen in FIG. 2, for example) at the second end 14b of the tubular suture 14 and creating a cinch for anchoring the suture 14 to the soft tissue. Once anchored, the suture 14 can be cut off near the anchor 22 and any remaining unused portion of the suture 14 can be discarded.

A method of manufacturing a medical device in accordance with the present disclosure can include forming a tubular wall 16 having a plurality or pores 20 and defining a hollow core 18, each pore 20 having a pore size that is greater than or equal to approximately 500 microns. Additionally, the method of manufacturing can include attaching a first end 14a of the tubular wall 14 to a surgical needle 12, such as that illustrated in FIG. 1. Forming the tubular wall 14 can include forming a tube from a mesh material. The tubular mesh wall 16 may be formed by directly weaving or knitting fibers into a tube shape. Alternatively, forming the tubular mesh wall 16 can include weaving or knitting fibers into a planar sheet and subsequently forming the planar sheet into a tube shape. Of course, other manufacturing possibilities exist and knitting and weaving fibers are not the only possibilities for creating a porous tube within the scope of the present disclosure, but rather, are mere examples.

Still further, a method of manufacturing a medical device 10 in accordance with the present disclosure can include providing an anchor 22 on an end of the tubular wall 16 opposite the needle 12. In some versions of the method, and as one example only, providing the anchor can be as simple as forming a loop, such as to resemble the anchor 22 depicted in FIG. 2.

Various modifications and variations of the described method and system of the disclosure will be apparent to those skilled in the art without departing from the scope and spirit of the disclosure. Although the disclosure has been described in connection with specific preferred embodiments, it should be understood that the disclosure as claimed should not be unduly limited to such specific embodiments. Indeed, various modifications of the described modes for carrying out the disclosure that are obvious to those skilled in the relevant fields are intended to be within the scope of the present disclosure.

We claim:

1. A method of re-apposing soft tissue, the method comprising:
   piercing a portion of the soft tissue with a surgical needle attached to a first end of an elongate mesh suture;
   threading the elongate mesh suture through the portion of soft tissue to make a plurality of stiches,
   wherein the elongate mesh suture comprises:
   a second end located away from the surgical needle;
   a flat wall having a length extending from the first end to the second end, and a cross-sectional rectangular shape with a uniform width and a uniform thickness that is smaller than the width; and
   a plurality of pores extending through the flat wall, wherein each of the plurality of pores has a pore diameter of approximately 200 microns to approximately 4 mm, such that the plurality of pores are adapted to accommodate the portion of soft tissue growing through the flat wall, thereby integrating with the elongate mesh suture.

2. The method of claim 1, wherein the thickness of the flat wall is approximately 0.1 mm to approximately 1 cm.

3. The method of claim 1, further comprising anchoring the elongate mesh suture in place in the portion of soft tissue after threading the elongate mesh suture through the portion of soft tissue.

4. The method of claim 3, wherein anchoring the elongate mesh suture in place comprises:
   passing the surgical needle through a closed loop anchor at the second end of the elongate mesh suture; and
   creating a cinch for anchoring the elongate mesh suture to the portion of soft tissue.

5. A method of re-apposing soft tissue, the method comprising:
   piercing a portion of the soft tissue with a surgical needle attached to a first end of an elongate mesh suture;
   threading the elongate mesh suture through the portion of soft tissue, wherein the elongate mesh suture comprises:
   a second end located away from the surgical needle;
   a flat wall having a length extending from the first end to the second end, and a cross-sectional rectangular shape with a uniform width and a uniform thickness that is smaller than the width; and
   a plurality of pores extending through the flat wall, wherein each of the plurality of pores has a pore diameter of approximately 200 microns to approximately 4 mm, such that the plurality of pores are adapted to accommodate the portion of soft tissue growing through the flat wall, thereby integrating with the elongate mesh suture; and
   anchoring the elongate mesh suture in place in the portion of soft tissue after threading the elongate mesh suture through the portion of soft tissue, wherein anchoring the elongate mesh suture in place comprises:
   passing the surgical needle through a closed loop anchor at the second end of the elongate mesh suture; and
   creating a cinch for anchoring the elongate mesh suture to the portion of soft tissue.

6. The method of claim 5, wherein threading the elongate mesh suture through the portion of soft tissue comprises making a plurality of stitches.

7. The method of claim 5, wherein the thickness of the flat wall is approximately 0.1 mm to approximately 1 cm.

* * * * *